United States Patent
Wang et al.

(10) Patent No.: US 12,195,784 B1
(45) Date of Patent: Jan. 14, 2025

(54) **METHOD FOR SCREENING *LACTOBACILLUS CASEI* FERMENTATION AGENT**

(71) Applicant: China Agricultural University, Beijing (CN)

(72) Inventors: Ran Wang, Beijing (CN); Huiyuan Guo, Beijing (CN); Pengjie Wang, Beijing (CN); Jingjing He, Beijing (CN); Xiaoxia Li, Beijing (CN); Liang Zhao, Beijing (CN); Bing Fang, Beijing (CN); Jing Zhan, Beijing (CN); Hao Zhang, Beijing (CN)

(73) Assignee: China Agricultural University, Beijing (CN)

( * ) Notice: Subject to any disclaimer, the term of this patent is extended or adjusted under 35 U.S.C. 154(b) by 0 days.

(21) Appl. No.: 18/673,376

(22) Filed: May 24, 2024

(30) Foreign Application Priority Data

Aug. 9, 2023 (CN) .......................... 202310993251.3

(51) Int. Cl.
| | |
|---|---|
| C12Q 1/40 | (2006.01) |
| C12N 1/20 | (2006.01) |
| C12Q 1/6851 | (2018.01) |
| A23C 9/12 | (2006.01) |
| C12Q 1/02 | (2006.01) |
| C12Q 1/6806 | (2018.01) |
| C12Q 1/686 | (2018.01) |
| C12R 1/245 | (2006.01) |

(52) U.S. Cl.
CPC .............. *C12Q 1/40* (2013.01); *C12N 1/205* (2021.05); *A23C 9/1206* (2013.01); *C12Q 1/025* (2013.01); *C12Q 1/6806* (2013.01); *C12Q 1/6851* (2013.01); *C12Q 1/686* (2013.01); *C12Q 2537/16* (2013.01); *C12R 2001/245* (2021.05); *C12Y 302/0108* (2013.01)

(58) Field of Classification Search
None
See application file for complete search history.

(56) References Cited

U.S. PATENT DOCUMENTS

| | | |
|---|---|---|
| 2015/0044330 A1 | 2/2015 | Heidtman et al. |
| 2019/0174773 A1 | 6/2019 | Loponen et al. |

FOREIGN PATENT DOCUMENTS

| | | | |
|---|---|---|---|
| CN | 104255930 A | 1/2015 | |
| CN | 108251334 A | * 7/2018 | ............... C12N 1/20 |
| CN | 115678873 A | 2/2023 | |

OTHER PUBLICATIONS

De Man et al. A Medium for the Cultivation of Lactobacilli. J. Appl. Bact. 23(1):130-135. (Year: 1960).*
Chen et al. Statistical Optimization of Novel Medium to Maximize the Yield of Exopolysaccharide from Lacticaseibacillus rhamnosus ZFM216 and its Immunomodulatory Activity. Frontiers in Nutrition 9:924495 (Year: 2022).*
Zotta et al. Selection of Lactiplantibacillus Strains for the Production of Fermented Table Olives. Microorganisms 10:625 (Year: 2022).*
Taskila et al. Comparison of Enrichment Media for Routine Detection of Beer Spoiling Lactic Acid Bacteria and Development of Trouble-shooting Medium for Lactobacillus backi. J. Inst. Brew. 116(2):151-156. (Year: 2010).*
Google Translation of CN108251334A (Year: 2018).*
Li et al. The plasmid-encoded lactose operon plays a vital role in the acid production rate of Lacticaseibacillus casei during milk beverage fermentation. Frontiers in Microbiology 13:1016904. (Year: 2022).*
Maria Jose Gosalbes, et al., Use of lac regulatory elements for gene expression in Lactobacillus casei, Lait 81, 2001, pp. 29-35.
Li Nan, et al., Probiotics and Development of Functional Yogurt: A Review of Recent Progress, Journal of Dairy Science and Technology, 2020, pp. 31-38, vol. 43 No. 3.
GB 5009.239-2016, Determination of food acidity, China National Standards, 2017, pp. 1-10, National Health and Family Planning Commission of the People's Republic of China.
GB 4789.35-2016, Food Safety National Standard Food Microbiology Test Lactobacillus test, China National Standards, 2017, pp. 1-8, National Health and Family Planning Commission of the People's Republic of China; State Food and Drug Administration.

* cited by examiner

*Primary Examiner* — Samuel C Woolwine

(57) ABSTRACT

A method for screening *Lactobacillus casei* fermentation agent is provided. The method is specifically implemented by screening a *Lactobacillus casei* strain with high-expression of a lac cluster gene and no enzymatic activity of β-fructosidase. The *Lactobacillus casei* strain that rapidly metabolizes lactose is screened through high expression of the lac cluster gene, such that the problem of large differences in acid production in fermented milk beverage products is avoided.

8 Claims, 5 Drawing Sheets

Specification includes a Sequence Listing.

SEQUENCE LISTING

```
Sequence total quantity: 4
SEQ ID NO: 1            moltype = DNA  length = 20
FEATURE                 Location/Qualifiers
misc_feature            1..20
                        note = The sequence is synthetized.
source                  1..20
                        mol_type = other DNA
                        organism = synthetic construct
SEQUENCE: 1
actggtcgtg gtacagttgc                                                20

SEQ ID NO: 2            moltype = DNA  length = 20
FEATURE                 Location/Qualifiers
misc_feature            1..20
                        note = The sequence is synthetized.
source                  1..20
                        mol_type = other DNA
                        organism = synthetic construct
SEQUENCE: 2
cacgaagcaa gacaccaacg                                                20

SEQ ID NO: 3            moltype = DNA  length = 25
FEATURE                 Location/Qualifiers
misc_feature            1..25
                        note = The sequence is synthetized.
source                  1..25
                        mol_type = other DNA
                        organism = synthetic construct
SEQUENCE: 3
agatggcatt gagacgacag attgg                                          25

SEQ ID NO: 4            moltype = DNA  length = 23
FEATURE                 Location/Qualifiers
misc_feature            1..23
                        note = The sequence is synthetized.
source                  1..23
                        mol_type = other DNA
                        organism = synthetic construct
SEQUENCE: 4
gtcactggca ccaacggata gtc                                            23
```

METHOD FOR SCREENING *LACTOBACILLUS CASEI* FERMENTATION AGENT

CROSS REFERENCE TO THE RELATED APPLICATIONS

This application is based upon and claims priority to Chinese Patent Application No. 202310993251.3, filed on Aug. 9, 2023, the entire contents of which are incorporated herein by reference.

Sequence Listing

The instant application contains a Sequence Listing which has been submitted in XML format via EFS-Web and is hereby incorporated by reference in its entirety. Said XML copy is named GBHCZHOO5_Sequence_Listing.xml, created on 04/24/2024, and is 5,962 bytes in size.

TECHNICAL FIELD

The present disclosure belongs to the technical field of microorganisms and food biotechnology, and specifically to a method for screening *Lactobacillus casei* fermentation agent.

BACKGROUND

Milk beverages are a very active part of the functional dairy industry. The global milk beverage market is valued at USD 13.9 billion by 2021, with fermented milk beverages being a leading product in the milk beverage market. The fermented milk beverages contain high levels of protein, calcium, and essential nutrients such as vitamin B and β-casein. The fermented milk beverages may relieve lactose indigestion and shortens rotavirus-induced diarrhea while preventing digestive system diseases such as constipation, improving immunity, and reducing infection risks.

Fermentation agent strains give the fermented milk beverages a rich flavor, slightly thicker texture, and unique aroma. At present, the fermented milk beverages are generally fermented by using Lactic acid bacteria (LAB) species as fermentation agents, such as *Lactobacillus, Streptococcus* and *Bifidobacterium*.

In the fermented milk beverages, the current methods for screening fermented milk beverage fermentation agents are mainly to perform screening according to a high acid production rate of single strains. In *Lactobacillus casei*, the factor primarily affecting an acid production rate of the *Lactobacillus casei* is the type of carbohydrates and sugar metabolism. The carbohydrates are fermented to form lactic acid, and the lactic acid, as a main end product, is or combined with other organic acids and alcohols. All types of *Lactobacillus casei* can use common hexose including glucose, fructose, mannose, and N-Acetyl-D-Glucosamine, and lactose, trehalose, and cellobiose. During sugar metabolism, as a hetero-fermentation strain, the way of the *Lactobacillus casei* to metabolize sugars is mediated by several pathways, including an ABC protein dependent system, a sugar permeability enzyme system, a sugar specific phosphoenolpyruvate dependent phosphotransferase (PTS) system, etc. However, the acidity of the fermented milk beverages is continuously increased due to excessive acid production. When the acidity is greater than 90° T, unacceptable oversourness of the fermented milk beverages appears due to an imbalance in the sweet-sour ratio, resulting in reduction in the taste of the milk beverages to reduce a survival rate of the *Lactobacillus casei* and induce a reduction in the stability of the fermented milk beverages, and thus shortening shelf life. In the *Lactobacillus casei*, the lactose enters cells through a gal-lac gene cluster of a phosphoenolpyruvate-lactose phosphotransferase system and is hydrolyzed into glucose and galactose. The glucose enters a glycolytic pathway or a pentose phosphate pathway via phosphofructokinase, aldolase, etc., and further decomposed into small molecule substances through acetaldehyde, ethanol, lactic dehydrogenase, etc.; the generated galactose is decomposed into organic acids under the action of a gene cluster galR-galKTEM. Lac cluster consists of lacTEGF genes, and lacG encodes phosphoric acid-β-galactosidase. Sucrose is transferred into the cells through a phosphoenolpyruvate-sucrose phosphotransferase system. The phosphorylated sucrose is hydrolyzed by β-fructosidase (EC 3.2.1.26) in the cells to generate glucose-6-phosphate and fructose, and the fructose is further guided to the glycolytic pathway through fructokinase.

It can be seen that lactose and sucrose metabolism genes can regulate the acid-producing capacity of *Lactobacillus casei* strains. However, there is a lack of correlational research of screening high-quality fermentation agents through genes related to lactose and sucrose metabolism. The *Lactobacillus casei* fermentation agents used domestically have the problem of large differences in acid production, mainly relying on foreign imports of *Lactobacillus casei* fermentation agents such as *L. casei*, Shirota, *L. casei* Danone and *L. casei* 01™ etc. at present. Therefore, how to screen *L. casei* suitable for fermented milk beverages is a technical problem to be solved in the art.

SUMMARY

For the problems of the existing technology, the present disclosure is intended to provide a targeted and efficient method for screening a *Lactobacillus casei* fermentation agent in a fermented milk beverage. The method is specifically implemented by screening a *Lactobacillus casei* strain with high-expression of a lac cluster gene and no enzymatic activity of β-fructosidase.

To achieve this purpose, the technical scheme of the present invention is as follows:

The first aspect of the present invention provides a method for screening a *Lactobacillus casei* fermentation agent. The method is specifically implemented by screening a *Lactobacillus casei* strain with high-expression of a lac cluster gene and no enzymatic activity of β-fructosidase, comprising the following steps:

(1) activating *Lactobacillus casei* to obtain *Lactobacillus casei* bacterial liquid;

Preferably, the operation step of step (1) comprises: inoculating the *Lactobacillus casei* into an MRS liquid culture medium according to a volume ratio of 1%, and culturing same at 37±1° C. to obtain the *Lactobacillus casei* bacterial liquid.

More preferably, the incubation time at 37° C.±1° C. was 8-16 h.

Further preferred, the incubation time at 37° C.±1° C. was 12 h.

(2) extracting total DNA from the *Lactobacillus casei*, amplifying tuf and lac cluster genes, using the tuf gene as a control, and using an equation Nrelatives=$(1+E)^{-\Delta C_T}$ to determine a plasmid copy number of the lac cluster gene;

Preferably, the lac cluster gene is a lacG gene.

Preferably, the step of using the equation Nrelatives=$(1+E)^{-\Delta C_T}$ to determine the plasmid copy number of the lacG in step (2) comprises:

using tuf2-F/R and lacG-F/R as primers, detecting a $C_T$ value through quantitative polymerase chain reaction (qPCR), and calculating expression levels of the tuf and lacG genes; and calculating the plasmid copy number through $\Delta C_T$.

The primer sequences are:
tuf2-F: 5'-ACTGGTCGTGGTACAGTTGC-3' (SEQ ID NO: 1),
tuf2-R: 5'-CACGAAGCAAGACACCAACG-3' (SEQ ID NO: 2);
and lacG-F/R:
lacG-F: 5'-AGATGGCATTGAGACGACAGATTGG-3' (SEQ ID NO: 3),
lacG-R: 5'-GTCACTGGCACCAACGGATAGTC-3' (SEQ ID NO: 4).

Preferably, the tuf gene is a gene of the elongation factor Tu of the single copy gene on the *Lactobacillus casei* genome (GenBank: AJ418937.2).

(3) preparing crude enzyme liquid of β-fructosidase, and determining enzymatic activity of the β-fructosidase of the *Lactobacillus casei*;

Further, the specific operation is: the *Lactobacillus casei* bacterial liquid prepared in step (2) is taken, inoculated in an S-MRS liquid culture medium at 1% addition by volume, and cultured at 37±1° C.; fermentation broth is taken, centrifugation is performed, 0.85% normal saline is added, well mixing is performed, centrifugation is performed, the 0.85% normal saline is added again, homogenization is performed for 3 times, for 15 s each time, and a strain is crushed to obtain crude enzyme liquid of the *Lactobacillus casei*; and the enzymatic activity of the β-fructosidase of the crude enzyme liquid of the *Lactobacillus casei* is determined.

More preferably, a method for determining the enzymatic activity of the β-fructosidase of the *Lactobacillus casei* comprises using tetramethylbenzidine as a substrate, and detecting a light absorption value of the crude enzyme liquid at a wavelength of 450 nm, wherein one enzyme unit is defined as an enzyme amount required to hydrolyze 1 μmol of the tetramethylbenzidine at 37° C. and pH 6.8 per minute.

(4) using the plasmid copy number of the lac cluster and the enzymatic activity of the (3-fructosidase as standards, and performing targeted screening on *Lactobacillus casei* fermentation agents.

In a second aspect, the present invention provides that an application of the screening method as stated in the first aspect in screening of a *Lactobacillus casei* fermentation agent.

Preferably, the *Lactobacillus casei* fermentation agent is used for preparing a flavored fermented yogurt, a milk beverage, or a cheese product.

The present disclosure has the following beneficial effects:

1. The *Lactobacillus casei* strain that rapidly metabolizes lactose is screened through high expression of the lac cluster gene, such that the problem of large differences in acid production in fermented milk beverage products is avoided.

2. By screening the *Lactobacillus casei* with no enzymatic activity of β-fructosidase, the *Lactobacillus casei* does not metabolize sucrose, such that post-acidification due to sucrose metabolism by the *Lactobacillus casei* is weakened (FIG. 3), and a centrifugation sedimentation rate of a fermented milk beverage is reduced (FIG. 5) to avoid phenomena of layering or whey precipitation.

3. Compared with a traditional screening method, by combining the lac cluster gene and 3-fructosidase to perform targeted screening on the *Lactobacillus casei* fermentation agent in the fermented milk beverage, the present disclosure has characteristics of efficient and specific screening, such that the oneness of the traditional screening method is avoided.

DETAILED DESCRIPTION OF THE EMBODIMENTS

Figure 1:
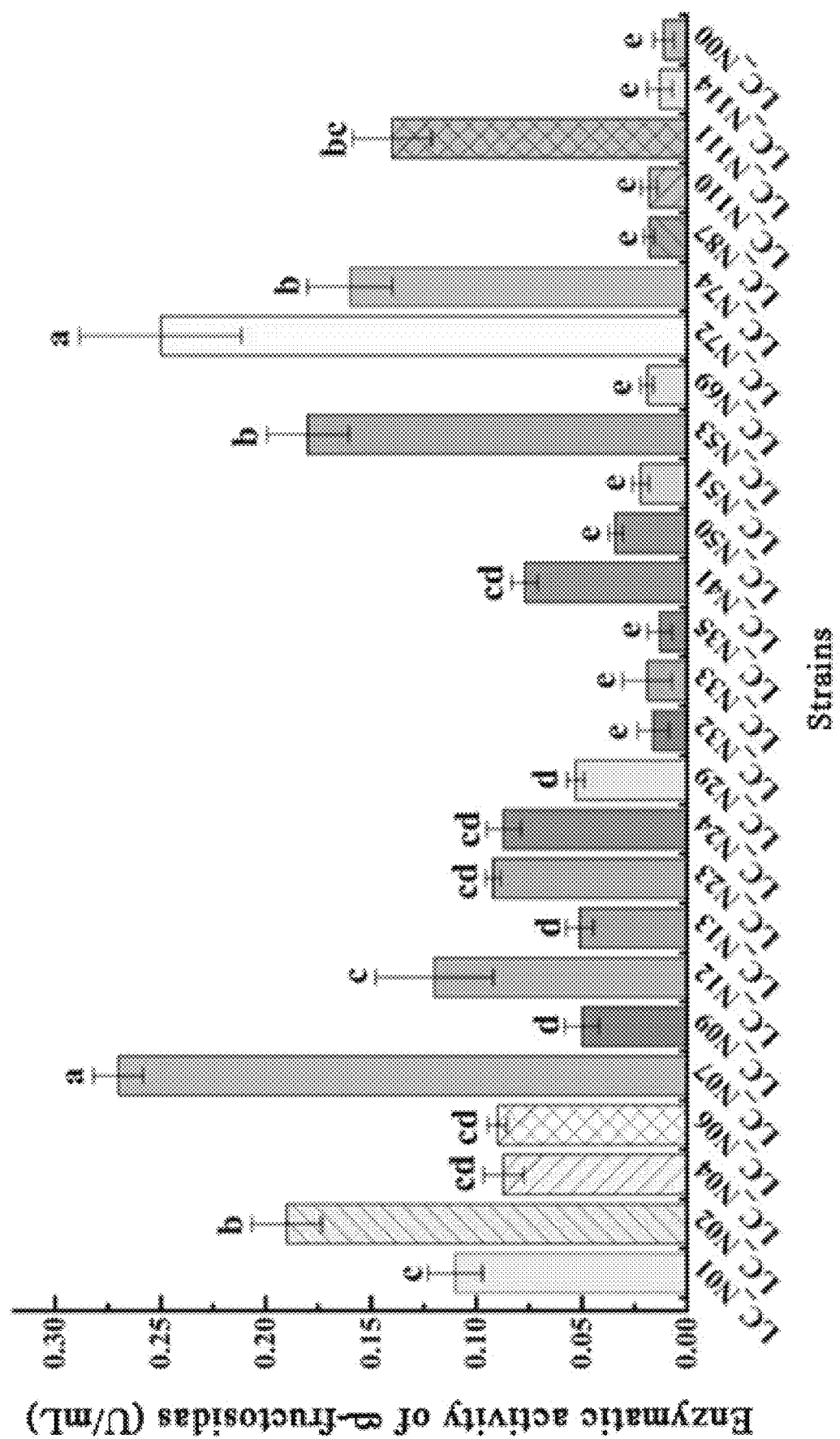
FIG. 1 is a comparison diagram of enzymatic activity of β-fructosidase of different *Lactobacillus casei* strains.

The implementation of the invention is not limited to the following embodiments, and any form of adaptations and/or changes made to the invention will fall into the scope of protection of the invention. In the present invention, all the equipment and raw materials can be purchased from the market or commonly used in the industry. Unless otherwise specified, the method used in the embodiment is a general technique in the field.

For numerical ranges, between endpoint values of each range, between endpoint values and individual point values, and individual point values may be combined to obtain one or more new numerical ranges, which shall be regarded as specifically disclosed herein.

Experimental Method:

Determination of a plasmid copy number: a qPCR is used, a single copy gene tuf on a *Lactobacillus casei* genome is used as a reference, and the plasmid copy number of a lacG of *Lactobacillus casei* is determined; primers tuf2-F and tuf2-R (tuf2-F:5'-ACTGGTCGTGGTACAGTTGC-3' shown in SEQ ID NO: 1 and tuf2-R:5'-CACGAAGCAA-GACACCAACG-3' shown in SEQ ID NO: 2) are used to amplify the tuf gene, and a qPCR reaction system (20 μL) includes the following: 9 μL of TB Green Premix Ex Taq (Tli RNaseH Plus), 1 μL 10 mmol/L of an upstream primer, 1 μL 10 mmol/L of a downstream primer, 2 μL of total DNA, and 7 μL of ultrapure water. qPCR reaction conditions include: 95° C., 5 min; [95° C., 20 s; 60° C., 30 s; 68° C., 30 s]×40 cycles, and detecting gene expression levels.

Using the tuf gene as a control, and using an equation Nrelatives=$(1+E)^{-\Delta C_T}$ to determine a plasmid copy number of the lac cluster; E is amplification efficiency, and E=$10^{-1/K}$, K is a standard curve slope; % efficiency=$(E-1)\times 100\%$; $\Delta C_T$ is a difference value in the number of cycles that fluorescent signals of amplified products of the lac cluster and tuf genes pass through when the fluorescent signals reach a set threshold.

Determination of enzymatic activity of β-fructosidase: β-fructosidase enzyme linked immunosorbent assay kits from Jiangsu Enzyme Immunoassay Industry Co., Ltd. are used. A 44 IU/L standard solution is diluted to 72, 36, 18, 9, and 4.5 IU/L by using standard diluent; and a blank well, a standard well, and a sample well to be tested are respectively set. 50 μL of a standard is added to an enzyme labeling coated plate, 40 μL of sample diluent is added to the sample hole to be tested, and then L of a sample to be tested is added. The sample is added to the enzyme labeling plate, and the enzyme labeling plate is gently shaken for well mixing; the enzyme labeling plate is sealed with a microplate sealer and then incubated at 37° C. for 30 min; liquid is discarded, washing liquid is filled in each well and is discarded after 30 s of standing, this operation is repeated for 5 times, and drying is performed through patting; 50 μL of an enzyme labeling reagent is added to each well, except for the blank well; the enzyme labeling plate is sealed with a microplate sealer and then incubated at 37° C. for 30 min; liquid is discarded, washing liquid is filled in each well and is discarded after 30 s of standing, this operation is repeated for 5 times, and drying is performed through patting; 50 μL of a color developing agent A is first added to each well, then 50 μL of a color developing agent B is added, well mixing is performed gently, and color development is performed in dark at 37° C. for 10 min; and Zeroing is performed with the blank well, and absorbance of the wells is measured in sequence at a wavelength of 450 nm; tetramethylbenzidine (TMB) serves as a substrate, one enzyme unit is defined as an enzyme amount required to hydrolyze 1 μmol of the TMB at 37° C. and pH 6.8 per minute.

Preparation of a Fermented Milk Beverage:

At S1, raw materials of 13% (w/v) of skimmed milk, 3% (w/v) of glucose, and 5% (w/v) of sucrose are mixed, dissolved at 50° C. for 30 min, and homogenized through 20 MPa; brown staining is performed at 95° C. for 4 hours; cooling is performed to 37° C.; and fermentation base material is obtained through preparation. *Lactobacillus casei* is inoculated in the fermentation base material according to an addition of $5\times10^6$ CFU/g, and is cultured for 96 h at 37° C., and 3 biological replicates are performed.

At S2, preparation of base material diluent: 14% (w/w) of white granulated sugar is dissolved in 70° C. water and fully stirred for 10 min, sterilization is performed for 5 min at 95° C., and base material diluent is prepared.

At S3, the base material and the base material diluent are mixed at a ratio of 1:3, and the fermented milk beverage is homogenized at 20-25 MPa and filled in an aseptic packaging bottle under aseptic conditions.

A fermented milk beverage was stored at 4° C. for 28 days. A method for detecting viable counts uses National standard GB 4789.35-2016 (National standard for food safety food microorganism test lactic acid bacteria test).

A method for detecting acidity uses National standard GB 5009.239-2016.

Detection of lactose and sucrose content: 0.2500 of a lactose standard and 0.2000 of a sucrose standard are accurately weighed and placed in a 100 mL volumetric flask, and are made up to 100 mL with ultrapure water; mass concentrations of lactose respectively are 2.5, 2, 1.5, 1, and 0.5 mg/mL; mass concentrations of sucrose respectively are 2, 1.8, 1.6, 1.4, 1.2, 1, 0.8, 0.6, 0.4, and 0.2 mg/mL; and a standard curve is plotted by using the concentrations of the standards as horizontal coordinates, and peak areas as longitudinal coordinates. 5.0 g of a fermented milk base (the fermentation base material) fermented for 96 hours is weighed and placed to a 100 mL beaker, 25.0 g of deionized water is added, and the mixture is fully dissolved by using a magnetic stirrer; 2.5 mL of a Carrez reagent 1 and 2.5 mL of a Carrez reagent 2 are added in sequence and are fully dissolved for 30 min; centrifugation is performed on the mixture for 15 min at 5000×g; supernatant is diluted to 100 mL with distilled water, and is filtered through a 0.22 μm membrane; and a Bio-Rad Aminex® HPX-87P (300 mm×7.8 mm×9 m) chromatographic column is combined with a 2414-type differential Refractive Index Detector (RID), a 5 mM sulfuric acid aqueous solution is used as a mobile phase, with a flow rate being 550 μL/min, a column temperature is set to 60° C., a sample size is 2 μL, and the lactose and the sucrose in samples are detected by using an external standard method. A formula of the Carrez reagent 1 includes: weighing 10.60 g of potassium ferrocyanide, and dissolving same to 100 mL with deionized water. A formula of the Carrez reagent 2 includes: weighing 21.90 g of zinc acetate dihydrate, dissolving same with the deionized water, adding 3 mL of acetic acid for dissolving, and making the mixture up to 100 mL.

Detection of a centrifugation sedimentation rate: a 50 mL centrifuge tube (mass being recorded as M) is taken, 20 mL of a fermented milk beverage (mass being recorded as M1) is weighed and centrifuged for 15 min at 4070×g, the centrifuge tube is inverted on a filter paper for 10 min, a bottom sediment (mass being recorded as M2) is weighed, and the centrifugation sedimentation rate is calculated according to centrifugation sedimentation rate=(M2-M)/(M1-M)×100%.

Embodiment 1: *Lactobacillus casei* Culture and Total DNA Extraction

*Lactobacillus casei* was inoculated in an MRS liquid culture medium according to a 1% (v/v) inoculation amount, and cultured at 37±1° C. in a stationary manner; when OD600=0.8-1.0, 2.5 mL of bacterial liquid was taken and centrifuged for 5 min at 4° C. and 12000×g, and supernatant was removed; 2 mL of a TES solution was added to resuspend the bacteria and centrifuged for 5 min at 4° C. and 12000×g, and supernatant was removed; 200 μL of 50 mg/mL lysozyme was added to resuspend the bacteria, and 200×g of the mixture was taken and digested for 1.5 h at 37° C.; 1 mL of a lysis solution was added, and gently mixed well, and the mixture was put in a water bath for 30 min at 65° C.; 400 μL of a 5 mol/L sodium chloride solution was added, and gently mixed well and centrifuged for 20 min at 4° C. and 13000×g; an equal volume of Tris saturated phenol-chloroform-isopentanol (25:24:1, pH >7.8) was added and well mixed and centrifuged for 10 min at 4° C. and 12000×g, and 1.5 mL of an upper aqueous phase solution was taken; 2 volumes of anhydrous ethanol and 0.1 volume of 3 mol/L sodium acetate were added, were subjected to precipitation for 2 h at −20° C. after well mixing, and were respectively filled in 1.5 mL centrifuge tubes and centrifuged for 15 min at 4° C. and 12000×g, and supernatant was removed; 1 mL of 70% pre-cooled ethanol was added to wash the precipitate and centrifuged for 10 min at 4° C. and 13000×g, and supernatant was removed; and 50 μL of an aqueous solution containing RNase was added to dissolve DNA, and the mixture was preserved at −20° C.

Embodiment 2: Plasmid Copy Number (PCN) Detection of Lac Cluster of *Lactobacillus casei*

Determination of a plasmid copy number: a qPCR is used, a single copy gene tuf on a *Lactobacillus casei* genome is used as a reference, and the plasmid copy number of a lacG of *Lactobacillus casei* is determined; primers tuf2-F and tuf2-R are used to amplify the tuf gene, and a qPCR reaction system (20 μL) includes the following:

9 μL of TB Green Premix Ex Taq (Tli RNaseH Plus), 1 μL 10 mmol/L of an upstream primer, 1 μL 10 mmol/L of a downstream primer, 2 μL of total DNA, and 7 μL of ultrapure water. qPCR reaction conditions include: 95° C., 5 min; [95° C., 20 s; 60° C., 30 s; 68° C., 30 s]×40 cycles, and detecting gene expression levels. Using the tuf gene as a control, and using an equation Nrelatives=$(1+E)^{-\Delta C_T}$ to determine a plasmid copy number of the lac cluster; E is amplification efficiency, and E=$10^{-1/K}$, K is a standard curve slope; % efficiency=(E−1)×100%; $\Delta C_T$ is a difference value in the number of cycles that fluorescent signals of amplified products of the lac cluster and tuf genes pass through when the fluorescent signals reach a set threshold.

The plasmid copy number of a lacG of the *Lactobacillus casei* was shown in Table 1, a commercial strain LC_N00 was used as a control, and the LC_N00 was *Lactobacillus casei* for fermentation purchased from Denmark Chr. Hansen. The plasmid copy numbers of the lacG in *Lactobacillus casei* LC_N111, N07, N51, N50, N02, N72, N32, N00, N33, N87, N23, N114, N12, N29, N35 and N110 respectively were 5.10, 4.93, 4.69, 4.31, 3.95, 3.95, 3.71, 3.29, 2.99, 2.51, 2.48, 2.41, 2.31, 2.28, 2.25 and 2.20 copy/cell, and the plasmid copy number of 15 *Lactobacillus casei* strains was significantly greater than that of other 10 *Lactobacillus casei* strains (p<0.05).

TABLE 1

| strain | $\Delta C_T$ | PCN |
|---|---|---|
| LC_N01 | 0.11 ± 0.03 | 1.08 ± 0.04$^f$ |
| LC_N02 | 1.98 ± 0.31 | 3.95 ± 1.11$^c$ |
| LC_N04 | 0.15 ± 0.03 | 1.11 ± 0.07$^f$ |
| LC_N06 | 0.25 ± 0.02 | 1.19 ± 0.08$^f$ |
| LC_N07 | 2.30 ± 0.27 | 4.93 ± 1.15$^a$ |
| LC_N09 | 0.17 ± 0.05 | 1.13 ± 0.12$^f$ |
| LC_N12 | 1.21 ± 0.12 | 2.31 ± 0.09$^{de}$ |
| LC_N13 | 0.11 ± 0.02 | 1.08 ± 0.14$^f$ |
| LC_N23 | 1.27 ± 0.38 | 2.41 ± 0.53$^{de}$ |
| LC_N24 | 0.17 ± 0.11 | 1.13 ± 0.10$^f$ |
| LC_N29 | 1.19 ± 0.08 | 2.28 ± 0.13d$^e$ |
| LC_N32 | 1.89 ± 0.31 | 3.71 ± 1.37$^c$ |
| LC_N33 | 1.58 ± 0.23 | 2.99 ± 0.89$^d$ |
| LC_N35 | 1.17 ± 0.02 | 2.25 ± 0.06$^e$ |
| LC_N41 | 0.28 ± 0.11 | 1.21 ± 0.35$^f$ |
| LC_N50 | 2.11 ± 0.03 | 4.31 ± 0.17$^{bc}$ |
| LC_N51 | 2.23 ± 0.15 | 4.69 ± 1.24$^b$ |
| LC_N53 | 0.20 ± 0.13 | 1.75 ± 0.25$^{ef}$ |
| LC_N69 | 1.27 ± 0.12 | 2.41 ± 0.40$^{de}$ |
| LC_N72 | 1.98 ± 0.26 | 3.95 ± 1.05$^c$ |
| LC_N74 | 0.29 ± 0.21 | 1.22 ± 0.74$^f$ |
| LC_N87 | 1.33 ± 0.12 | 2.51 ± 0.22$^{de}$ |
| LC_N110 | 1.14 ± 0.30 | 2.20 ± 0.58$^e$ |
| LC_N111 | 2.35 ± 0.66 | 5.10 ± 1.18$^a$ |
| LC_N114 | 1.31 ± 0.09 | 2.48 ± 0.27$^{de}$ |
| LC_N00 | 1.72 ± 011 | 3.29 ± 0.35$^d$ |

Embodiment 3: Determination of Enzymatic Activity of β-Fructosidase of *Lactobacillus casei*

*Lactobacillus casei* was inoculated in an MRS liquid culture medium according to a 1% (v/v) inoculation amount, and cultured for 12 h at 37±1° C.; the strain was inoculated in an S-MRS liquid culture medium according to a 1% (v/v) inoculation amount, and cultured for 12 h at 37±1° C.; 10 mL of fermentation broth was taken and centrifuged for 5 min and 12000×g; 10 mL of 0.85% normal saline was added, and washed the bacteria after being well mixed and centrifuged for 5 min and 12000×g; and 1 mL of 0.85% normal saline was added, homogenization was performed for 15 s for 3 times, the strain was crushed, and prepared crude enzyme liquid was placed on ice.

A 44 IU/L standard solution is diluted to 72, 36, 18, 9, and 4.5 IU/L by using standard diluent; and a blank well, a standard well, and a sample well to be tested are respectively set. 50 μL of a standard is added to an enzyme labeling coated plate, 40 μL of sample diluent is added to the sample hole to be tested, and then 10 μL of a sample to be tested is added. The sample is added to the enzyme labeling plate, and the enzyme labeling plate is gently shaken for well mixing; the enzyme labeling plate is sealed with a microplate sealer and then incubated at 37° C. for 30 min; liquid is discarded, washing liquid is filled in each well and is discarded after 30 s of standing, this operation is repeated for 5 times, and drying is performed through patting; 50 μL of an enzyme labeling reagent is added to each well, except for the blank well; the enzyme labeling plate is sealed with a microplate sealer and then incubated at 37° C. for 30 min; liquid is discarded, washing liquid is filled in each well and is discarded after 30 s of standing, this operation is repeated for 5 times, and drying is performed through patting; 50 μL of a color developing agent A is first added to each well, then 50 μL of a color developing agent B is added, well mixing is performed gently, and color development is performed in dark at 37° C. for 10 min; and Zeroing is performed with the blank well, and absorbance of the wells is measured in sequence at a wavelength of 450 nm; tetramethylbenzidine (TMB) serves as a substrate, one enzyme unit is defined as an enzyme amount required to hydrolyze 1 μmol of the tetramethylbenzidine at 37° C. and pH 6.8 per minute.

The enzymatic activity of β-fructosidase of the *Lactobacillus casei* was shown in FIG. 1, and the enzymatic activity of the β-fructosidase of the *Lactobacillus casei* LC_N07, N72, N02, N53, N74, N111, N12 and N01 was 0.271, 0.252, 0.194, 0.183, 0.164, 0.139, 0.122 and 0.113 U/mL, respectively; and the strains with the lowest enzymatic activity of the β-fructosidase were N50, N51, N33, N69, N87, N110, N32, N35, N114 and LC_N00.

Embodiment 4: Determination of Acidity of Fermented Milk Beverage Containing *Lactobacillus casei*

Raw materials of 13% (w/v) of skimmed milk, 3% (w/v) of glucose, and 5% (w/v) of sucrose are mixed, dissolved at 50° C. for 30 min, and homogenized through 20 MPa; brown staining is performed at 95° C. for 4 hours; cooling is performed to 37° C.; and fermentation base material is obtained through preparation. *Lactobacillus casei* is inoculated in the fermentation base material according to an addition of 5×10$^6$ CFU/g, and is cultured for 96 h at 37° C., and 3 biological replicates are performed.

Preparation of base material diluent: 14% (w/w) of white granulated sugar is dissolved in 70° C. water and fully stirred for 10 min, sterilization is performed for 5 min at 95° C., and base material diluent is prepared.

The base material and the base material diluent are mixed at a ratio of 1:3, and the fermented milk beverage is homogenized at 20-25 MPa and filled in an aseptic packaging bottle under aseptic conditions.

Figure 2:
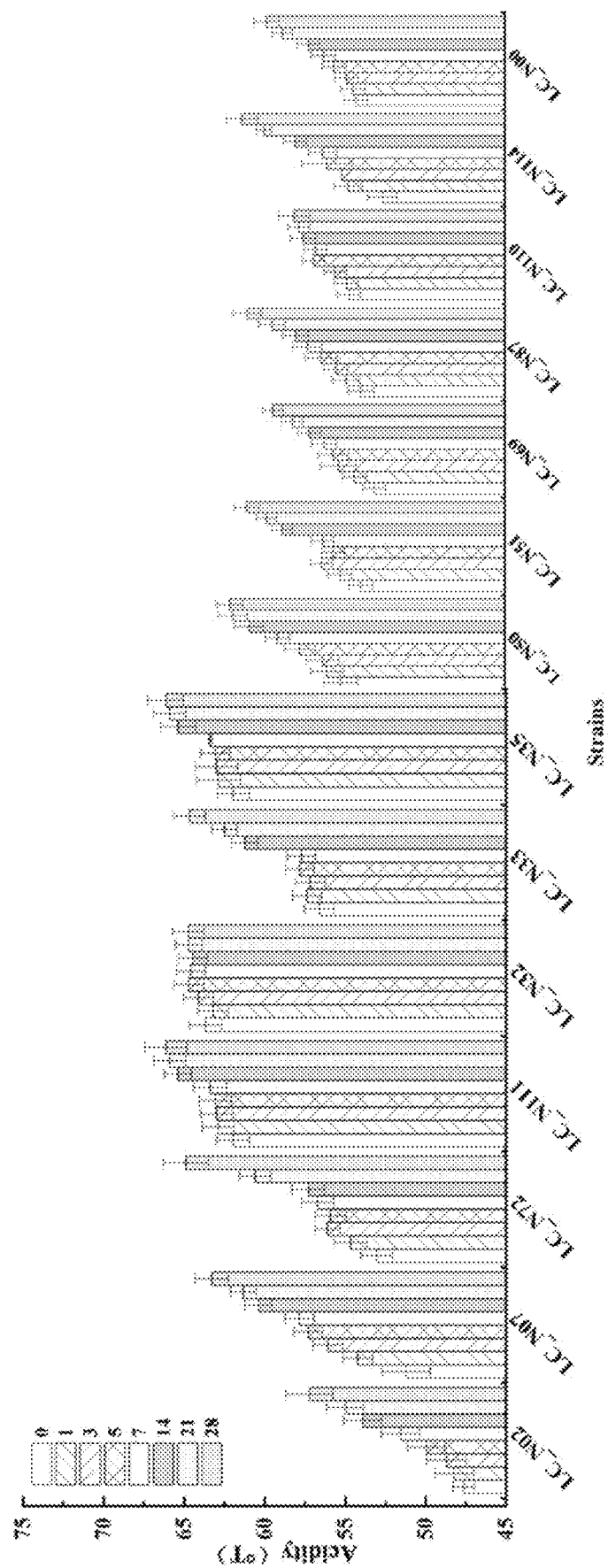
FIG. 2 is a comparison diagram of acidity of fermented milk beverages containing different types of *Lactobacillus casei* within shelf life.

A fermented milk beverage was stored at 4° C. for 28 days, and the acidity of *Lactobacillus casei* within shelf life was detected. The acidity of the fermented milk beverage containing the *Lactobacillus casei* within shelf life was shown in FIG. 2. At Day 0, the acidity of LC_N02 was the lowest (47.63° T), and the acidity of LC_N72, N35, and N111 was the highest at Day 0 (63.69, 61.69, and 61.96° T); and at Day 28, the acidity of LC_N02 was the lowest at Day 28 (57.21° T), and the acidity of LC_N35, N50, and N111 was the highest at Day 28 (66.10, 66.14, and 66.16° T). In post-acidification, the acidity of LC_N07, N72, and N111 during storage was greater than 10° T.

Embodiment 5: Determination of Viable Count of Fermented Milk Beverage Containing *Lactobacillus casei*

Figure 3:
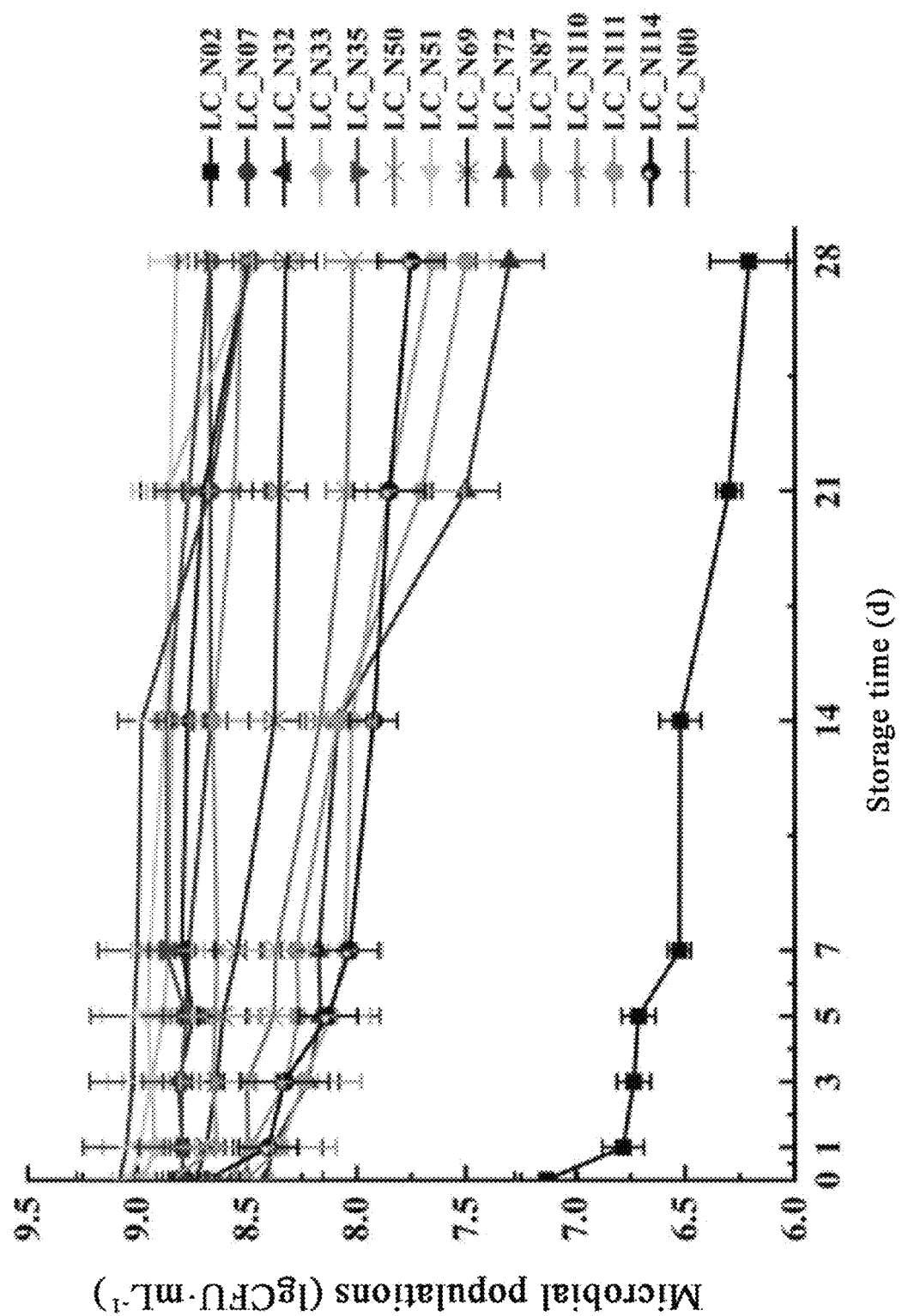
FIG. 3 is a comparison diagram of changes in microbial populations in fermented milk beverages containing different types of *Lactobacillus casei* within shelf life.

Other details were the same as Embodiment 4, and a difference between this embodiment and other embodiments lies in that change in a viable count of *Lactobacillus casei* in a fermented milk beverage within shelf life were detected. The viable count of the *Lactobacillus casei* within shelf life was shown in FIG. 3. At Day 0, the viable counts of LC_N00 and LC_N51 (9.08 and 9.03) were the highest, the viable counts of LC_N72 and LC_N02 (8.41 and 7.13) were the lowest; and after 28 days of storage, the viable counts of LC_N07, N32, N35, N51, N110 and N00 (8.67, 8.50, 8.67, 8.82, 8.52 and 8.49) were the highest, and the viable count of LC_N02 (6.21) was the lowest. The strain with the smallest change in viable count within shelf life was LC_N32, N35, N51 and N110 (0.29, 0.13, 0.21 and 0.33).

Embodiment 6: Determination of Utilization of Lactose and Sucrose by *Lactobacillus casei*

The fermentation base material in Embodiment 4 was taken for lactose and sucrose determination.

0.2500 of a lactose standard and 0.2000 of a sucrose standard are accurately weighed and placed in a 100 mL volumetric flask, and are made up to 100 mL with ultrapure water; mass concentrations of lactose respectively are 2.5, 2, 1.5, 1, and 0.5 mg/mL; mass concentrations of sucrose respectively are 2, 1.8, 1.6, 1.4, 1.2, 1, 0.8, 0.6, 0.4, and 0.2 mg/mL; and a standard curve is plotted by using the concentrations of the standards as horizontal coordinates, and peak areas as longitudinal coordinates.

5.0 g of a fermented milk base (the fermentation base material) fermented for 96 hours is weighed and placed to a 100 mL beaker, 25.0 g of deionized water is added, and the mixture is fully dissolved by using a magnetic stirrer; 2.5 mL of a Carrez reagent 1 and 2.5 mL of a Carrez reagent 2 are added in sequence and are fully dissolved for 30 min; centrifugation is performed on the mixture for 15 min at 5000×g; supernatant is diluted to 100 mL with distilled water, and is filtered through a 0.22 μm membrane; and a Bio-Rad Aminex® HPX-87P (300 mm×7.8 mm×9 μm) chromatographic column is combined with a 2414-type differential Refractive Index Detector (RID), a 5 mM sulfuric acid aqueous solution is used as a mobile phase, with a flow rate being 550 μL/min, a column temperature is set to 60° C., a sample size is 2 μL, and the lactose and the sucrose in samples are detected by using an external standard method.

A formula of the Carrez reagent 1 includes: weighing 10.60 g of potassium ferrocyanide, and dissolving same to 100 mL with deionized water. A formula of the Carrez reagent 2 includes: weighing 21.90 g of zinc acetate dihydrate, dissolving same with the deionized water, adding 3 mL of acetic acid for dissolving, and making the mixture up to 100 mL.

Figure 4:
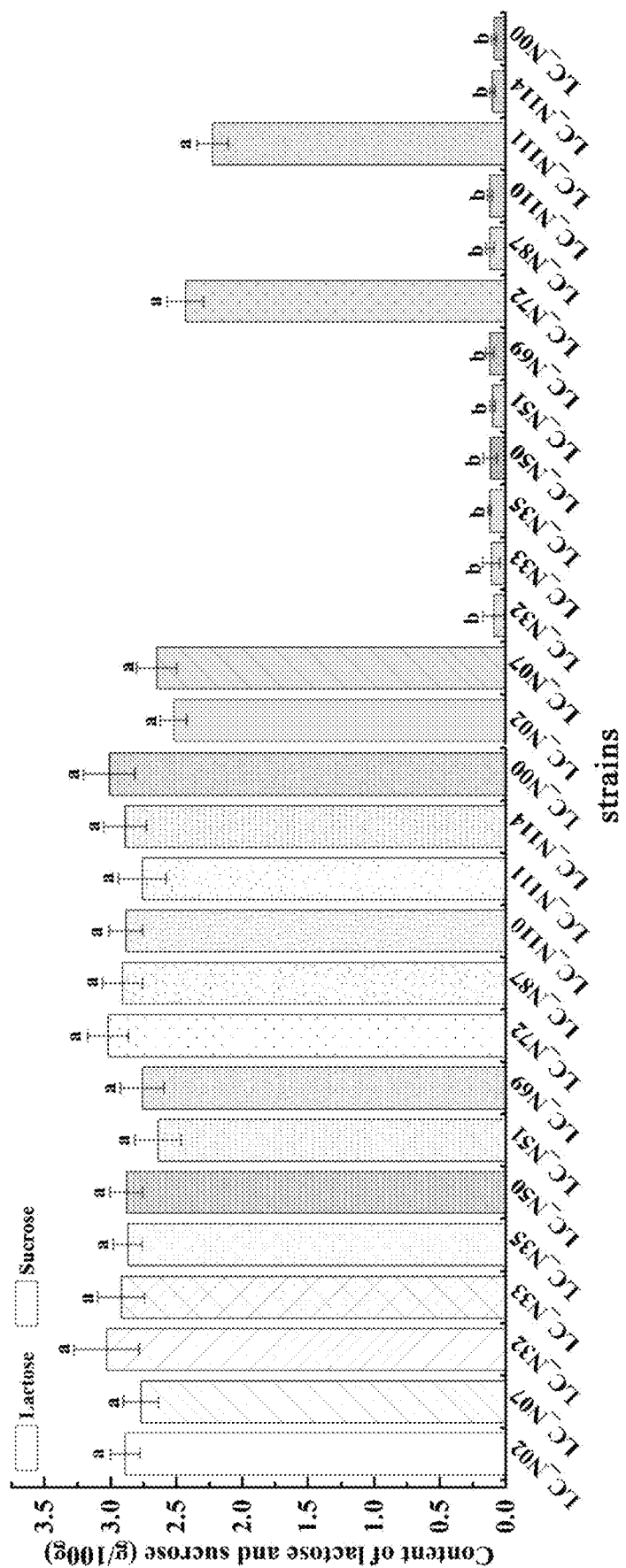
FIG. 4 is a variation diagram of content of sucrose and lactose in fermented milk beverages containing different types of *Lactobacillus casei* within shelf life.

Utilization of lactose and sucrose by *Lactobacillus casei* was shown in FIG. 4. The utilization of the lactose by all types of *Lactobacillus casei* was greater than 50%, and there was no significant differences between the strains; in the utilization of the sucrose, the utilization of the sucrose by LC_N02, N07, N72 and N111 was 51%, 53.6%, 49.2% and 45% respectively, the utilization of the sucrose by the four strains was significantly greater than that by LC_N32, N33, N35, N51, N69, N87, N110, N114 and N00, indicating that there was no significant difference in the capabilities of all strains to metabolize the lactose, while LC_N02, N07, N72 and N111 were able to rapidly utilize the sucrose, and the other 9 strains and the commercial strain LC_N00 did not utilize the sucrose.

Embodiment 7: Determination of Centrifugation Sedimentation Rate of Fermented Milk Beverage Containing *Lactobacillus casei*

Other details were the same as Embodiment 4, and a difference between this embodiment and other embodiments lies in that change in centrifugation sedimentation rate of fermented milk beverage containing *Lactobacillus casei*.

Figure 5:
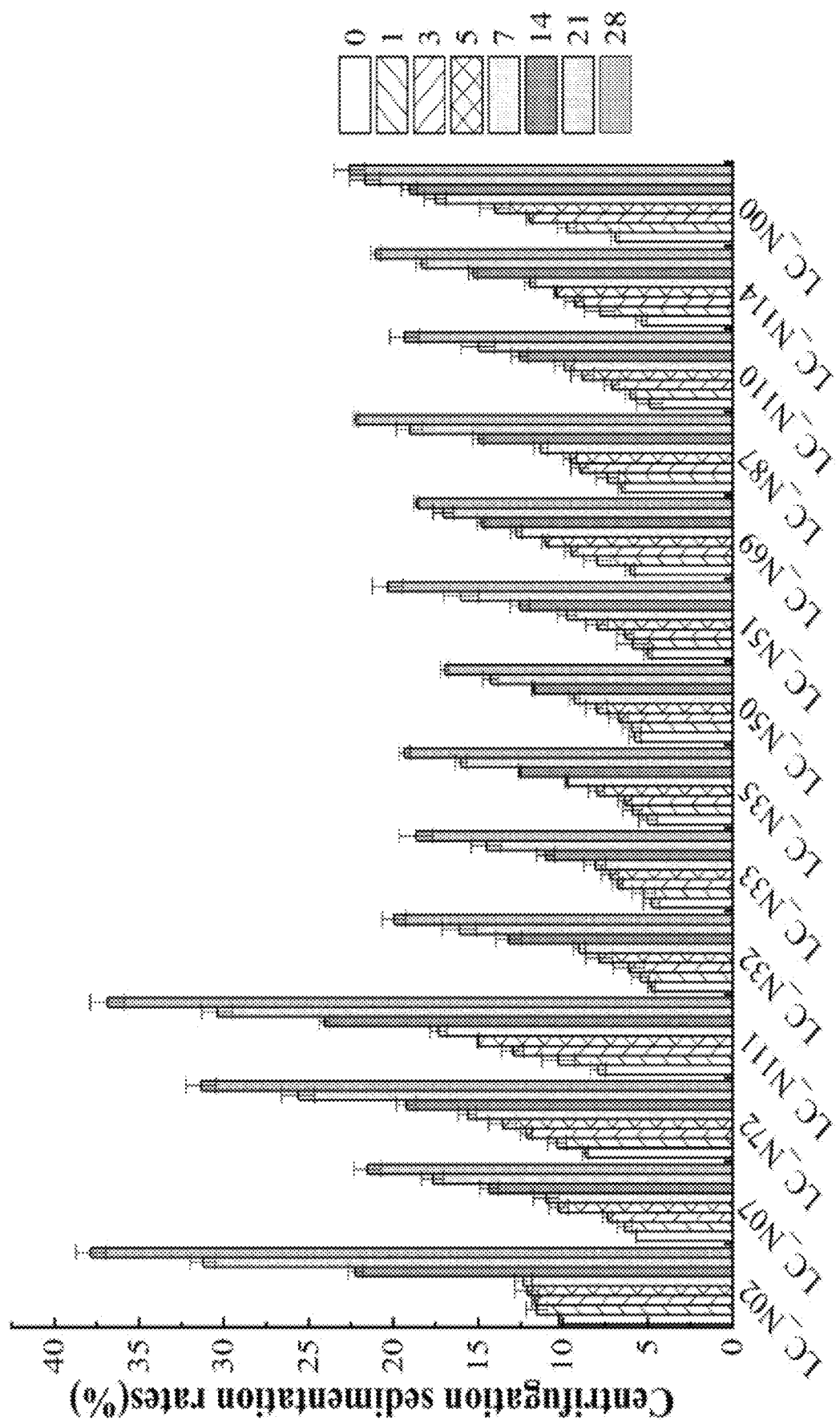
FIG. 5 is a comparison diagram of centrifugation sedimentation rates of fermented milk beverages containing different types of *Lactobacillus casei* within shelf life.

Detection of a centrifugation sedimentation rate: a 50 mL centrifuge tube (mass being recorded as M) is taken, 20 mL of a fermented milk beverage (mass being recorded as M1) is weighed and centrifuged for 15 min at 4070×g, the centrifuge tube is inverted on a filter paper for 10 min, a bottom sediment (mass being recorded as M2) is weighed, and the centrifugation sedimentation rate is calculated according to centrifugation sedimentation rate=(M2-M)/(M1-M)×100%. A centrifugation sedimentation rate of a fermented milk beverage within shelf life was shown in FIG. 5. At Day 28 of storage, LC_N32, N33, N35, N50, N51, N69, N87, N110 and N114 respectively were 19.96%, 18.66%, 19.34%, 16.97%, 20.34%, 18.63%, 22.21%, 19.34% and 21.04%, which were significantly lower than LC_N02, LC_N72, and LC_N111.

The plurality of types of *Lactobacillus casei* were screened according to the plasmid copy number of the lacG and the enzymatic activity of the β-fructosidase; and through determination of the acidity, viable count, lactose-sucrose utilization rate, and centrifugation sedimentation rate of the fermented milk beverage, it was found that the *Lactobacillus casei* strains LC_N32, N33, N35, N50, N51, N69, N87, N110 and N114 screened according to screening indicators had the above excellent characteristics.

The acidity, viable count, lactose and sucrose content, and centrifugation sedimentation rate of the fermented milk beverage within shelf life were evaluated. The acidity of milk beverages prepared by the 9 screened strains and stored for 28 days was 64° T, a microbial population was greater than 7.5 lgCFU/g, and the centrifugation sedimentation rate was less than 15.67%, indicating that the strains screened based on the plasmid copy number of the lacG and the enzymatic activity of the (3-fructosidase were able to be used as a fermentation agent to ferment the milk beverages.

In summary, the method for screening a *Lactobacillus casei* fermentation agent that was established based on the ferment the milk beverages with high-expression of the lac cluster gene and no enzymatic activity of the β-fructosidase was characterized by high efficiency and specificity screening, such that the strains were guaranteed to rapidly metabolize the lactose, post-acidification due to sucrose metabolism by the *Lactobacillus casei* was weakened, and the centrifugation sedimentation rate of the fermented milk beverage was reduced to avoid phenomena of layering or whey precipitation.

What is claimed is:

1. A method for screening a *Lactobacillus casei* fermentation agent, comprising the following steps:
   (1) inoculating *Lactobacillus casei* into a liquid culture medium and culturing to obtain an inoculated *Lactobacillus casei* liquid culture medium;
   (2) extracting a total DNA from the *Lactobacillus casei*, amplifying a tuf gene and a lac cluster gene, using the tuf gene as a control, and using an equation Nrelatives= $(1+E)^{-\Delta C_T}$ to determine a plasmid copy number of the lac cluster gene, wherein the tuf gene is an elongation factor Tu of a single copy gene on a *L. casei* genome; Nrelatives is a plasmid copy number;
   E is an amplification efficiency, and $E=10^{-1/K}$, K is a standard curve slope;
   $-\Delta C_T$ is a difference value between a number of a first cycle and a number of a second cycle, wherein a fluorescent signal of an amplified product of the lac cluster gene reaches a set threshold through the first cycle, a fluorescent signal of an amplified product of the tuf gene reaches the set threshold through the second cycle;
   the tuf gene is a gene of an elongation factor Tu of a single copy gene on a *Lactobacillus casei* genome, and a GenBank number of the tuf gene is AJ418937.2; and the lac cluster gene is a lacG gene; wherein
   the step of using the equation Nrelatives= $(1+E)^{-\Delta C_T}$ to determine a plasmid copy number of the lacG gene in the step (2) comprises:
   using tuf2-F/R:
   tuf2-F: SEQ ID NO: 1,
   tuf2-R: SEQ ID NO: 2;
   and lacG-F/R:
   lacG-F: SEQ IS NO: SEQ ID NO: 3,
   lacG-R: SEQ ID NO: 4 as primers, detecting a $C_T$ value through a quantitative polymerase chain reaction (qPCR), and calculating expression levels of the tuf gene and lacG gene; and calculating the plasmid copy number through the $\Delta C_T$;
   (3) preparing a crude enzyme liquid of β-fructosidase, and determining an enzymatic activity of the β-fructosidase of the *Lactobacillus casei*; and
   (4) performing a screening on the *Lactobacillus casei* fermentation agent according to the plasmid copy number of the lacG gene and the enzymatic activity of the β-fructosidase.

2. The method according to claim 1, wherein the step (1) comprises: inoculating the *Lactobacillus casei* into a liquid culture medium according to a volume ratio of 1%, and culturing at 37±1° C. to obtain the inoculated *Lactobacillus casei* liquid culture medium.

3. An application of the screening method according to claim 2, wherein the *Lactobacillus casei* fermentation agent is used for preparing a flavored fermented yogurt, a milk beverage, or a cheese product.

4. The method according to claim 1, wherein the step (3) comprises: taking and inoculating the *Lactobacillus casei* liquid culture medium prepared in the step (1) in a second liquid culture medium at 1% addition by volume, and culturing at 37±1° C. to produce a fermentation broth; taking and centrifugating the fermentation broth, followed by adding a first 0.85% normal saline for a well mixing, centrifugating a resulting mixture, followed by adding a second 0.85% normal saline, to perform a homogenization for 3 times, with 15 s each time, and crushing a strain to obtain a crude enzyme liquid of the *Lactobacillus casei*; and determining an enzymatic activity of β-fructosidase of the crude enzyme liquid of the *Lactobacillus casei*.

5. The method according to claim 4, wherein a method for determining the enzymatic activity of the β-fructosidase of the *Lactobacillus casei* comprises using 3-3'-5-5'-tetramethylbenzidine as a substrate, detecting a light absorption value of the crude enzyme liquid at a wavelength of 450 nm, wherein an enzyme unit is defined as an enzyme amount required to hydrolyze 1 μmol of the 3-3'-5-5'-tetramethylbenzidine at 37° C. and a pH of 6.8 per minute.

6. An application of the screening method according to claim 5, wherein the *Lactobacillus casei* fermentation agent is used for preparing a flavored fermented yogurt, a milk beverage, or a cheese product.

7. An application of the screening method according to claim 4, wherein the *Lactobacillus casei* fermentation agent is used for preparing a flavored fermented yogurt, a milk beverage, or a cheese product.

8. An application of the screening method according to claim 1, wherein the *Lactobacillus casei* fermentation agent is used for preparing a flavored fermented yogurt, a milk beverage, or a cheese product.

* * * * *